US012558023B2

(12) United States Patent
Wang

(10) Patent No.: US 12,558,023 B2
(45) Date of Patent: Feb. 24, 2026

(54) DEVICE FOR ESTABLISHING AN AMNIOTIC CAVITY ACCESS THROUGH A MOTHER AND METHOD THEREOF

(71) Applicant: Xiamen Brana Design Co., Ltd., Xiamen (CN)

(72) Inventor: Zhongtang Wang, Xiamen (CN)

(73) Assignee: Xiamen Brana Design Co., Ltd., Xiamen (CN)

( * ) Notice: Subject to any disclaimer, the term of this patent is extended or adjusted under 35 U.S.C. 154(b) by 479 days.

(21) Appl. No.: 18/070,439

(22) Filed: Nov. 28, 2022

(65) Prior Publication Data

US 2023/0165516 A1 Jun. 1, 2023

(51) Int. Cl.
*A61B 5/00* (2006.01)
*A61B 10/00* (2006.01)
*A61M 29/02* (2006.01)

(52) U.S. Cl.
CPC ........ *A61B 5/4337* (2013.01); *A61B 10/0048* (2013.01); *A61M 29/02* (2013.01)

(58) Field of Classification Search
CPC ... A61B 5/4337; A61B 10/0048; A61M 29/02
See application file for complete search history.

(56) References Cited

U.S. PATENT DOCUMENTS

| | | | | |
|---|---|---|---|---|
| 3,410,269 A | * | 11/1968 | Hovick | A61B 17/4208 606/125 |
| 4,280,508 A | * | 7/1981 | Barrada | A61B 17/4208 600/549 |
| 2002/0120252 A1 | * | 8/2002 | Brock | A61B 90/36 606/1 |
| 2009/0069634 A1 | * | 3/2009 | Larkin | A61B 1/303 600/222 |
| 2011/0112434 A1 | * | 5/2011 | Ghabrial | A61B 1/00154 606/41 |
| 2021/0307780 A1 | * | 10/2021 | Quintero | A61B 17/4208 |

* cited by examiner

*Primary Examiner* — Richard G Louis
(74) *Attorney, Agent, or Firm* — David & Raymond Patent Firm; Raymond Y Chan

(57) ABSTRACT

A device for making an amniotic cavity access through a mother and method thereof is disclosed, which includes a transvaginal fetal membrane puncture assembly configured to construct the amniotic cavity access through a natural orifice of a maternal vagina, a trans maternal abdominal wall uterine fetal member puncture assembly configured to construct the amniotic cavity access through the maternal abdominal wall and/or a belly button, and an amniotic cavity combined sheath configured to form the amniotic cavity access for placing a fetus positioning surgical robotic arm and/or surgical instruments, thereby providing a safe operation channel for the implementation of an intrauterine fetal minimally invasive surgery.

13 Claims, 12 Drawing Sheets

DEVICE FOR ESTABLISHING AN AMNIOTIC CAVITY ACCESS THROUGH A MOTHER AND METHOD THEREOF

CROSS REFERENCE OF RELATED APPLICATION

This application is a non-provisional application that claims the benefit of priority under 35 U.S.C. § 119 to a Chinese application, application number 202111426867.X, filed Nov. 28, 2021, and a Chinese application number 202111426866.5, filed Nov. 28, 2021, which are incorporated herewith by reference in their entirety.

BACKGROUND OF THE PRESENT INVENTION

Field of Invention

The application relates to a field of a medical device, in particular to a device for making an amniotic cavity access through a mother and method thereof.

Description of Related Arts

The incidence of a fetal birth defect is 4%-6%, and the birth defect has become an important global public health and social problem. Compared with a congenital deformity correction after birth, an intrauterine surgery to correct the congenital deformity has many advantages, including a maternal placenta being able to provide safe support for a fetus, avoiding intrauterine growth delay or death, less obvious scars in a surgical area, and reducing a family psychological and financial burden.

Fetoscopic surgery is only suitable for intrauterine treatment of a few congenital defects, such as a twin-twin transfusion syndrome, a drainage, and an intrauterine blood transfusion. Slightly more complex congenital defects, such as a tumor a diaphragmatic hernia, a myelomeningocele, an exposed internal organ, a cleft lip and palate, usually require to dissect a uterus, take out the fetus, and return the fetus to the uterus after surgery.

Clinical data over the past 30 years have shown that the intrauterine surgery to correct the congenital deformity is unsatisfactory because of a high incidence of a premature birth due to a postoperative placental abruption and a maternal uterine contraction.

The Intrauterine Surgery at Least Includes a Plurality of Shortcomings as Follow:

(1) A cesarean section, loss of an amniotic fluid and part of the fetus leaving the uterus will cause severe trauma to the uterus and easily induce the maternal uterine contraction.

(2) During the cesarean section, a placenta is inevitable damaged, resulting in a damage to the placenta and easy induction of the postoperative placental abruption.

(3) The fetus completely or partially leaves the uterus, which makes the fetus out of a safety protection of the uterus and the amniotic fluid, resulting in a potential damage to the fetus.

(4) Although a laparoscopic surgery can reduce an abdominal and uterine trauma, the fetus floats in the uterus, which makes it difficult to reveal the defect or deformity, thereby increasing the intrauterine surgery difficulty.

Constructing an intrauterine surgical access through the mother, such as a natural orifice vaginal cervix, a navel or abdominal wall one-bore and/or two-bore channel, can avoid or reduce the damage to the uterus and placenta, thereby reducing the premature birth incidence due to the postoperative placental abruption, and/or the maternal uterine contraction.

In addition, a surgical robot can be used to perform the intrauterine surgery. The surgical robot carries a surgical instrument into the amniotic cavity through a vaginal cervical canal or abdominal wall, adjusts and fixes the fetal position, and fully exposes a surgical vision. Therefore, the fetus does not need to leave the uterus and amniotic fluid environment during the intrauterine surgery, avoiding the potential damage to the fetus, thereby reducing the occurrence of premature birth caused by the postoperative placental abruption and the maternal uterine contraction.

SUMMARY OF THE PRESENT INVENTION

A medical device is provided for making the amniotic cavity access for a fetal intrauterine surgical treatment via the vaginal cervical canal, the navel or the abdominal wall.

According to an embodiment of the present invention, a device for establishing a trans-maternal amniotic cavity access is configured to make a trans-maternal amniotic cavity passage to provide an operation pathway for performing minimally invasive fetal intrauterine surgery. The device comprises a trans-maternal vaginal fetal membrane puncture assembly configured to construct a trans vaginal amniotic cavity access, and a trans umbilical or abdominal puncture assembly configured to construct a trans umbilical or abdominal amniotic cavity access.

According to an embodiment of the present invention, the trans-maternal vaginal fetal membrane puncture assembly comprises a vaginal speculum, a cervical dilator, a fetal membrane puncture instrument, and a vaginal cervical dilator. Wherein, the vaginal speculum includes a hand-held vaginal dilator and a light source module, which is configured to expand a vagina and perform a cervical dilation operation under a direct vision. The cervical dilator includes a cervical dilation rod and a balloon module, which is configured to improve the efficiency of a cervical dilation. The fetal membrane puncture instrument includes a self-tapping thread configured to control an advancing distance and assist the vaginal cervical dilator to be inserted into the amniotic cavity. The vaginal cervical dilator includes a combined sheath, a one-way valve, and a fastening component for establishing a passage through the vagina, cervix, and fetal membrane, the one-way valve is configured for preventing an outflow of amniotic fluid, the fastening component is configured for connection with an operating table bracket to stabilize the vaginal cervical dilator.

Preferably, the light source module comprises a battery, a light-emitting diode (LED) lamp, a circuit, and a switch. The switch can be arranged on a handle of the hand-held vaginal dilator, the number of LED lamp can be multiple, and the LED lamp can also be replaced by a cold light source light.

Preferably, the light source module can be connected to the hand-held vaginal dilator in a detachable coupling manner, so that a conventional hand-held vaginal dilator can be used to make the vaginal speculum.

Preferably, the balloon module comprises a balloon body, a pipeline, and an injection pot. The balloon body can be wrapped around and fixed on the cervical dilation rod. The cervical dilation rod includes a hand-held part and a cervical dilation part. The diameter of cervical dilation part is not more than 3 mm. The injection pot is configured for connecting a syringe needle.

Preferably, the fetal membrane puncture instrument comprises a handle and a puncturing part. The puncture part is conical with self-tapping threads which spacing is close to a thickness of the fetal membrane wall, usually from 0.1 mm to 0.25 mm.

Preferably, the combined sheath comprises a vaginal segment sheath, a cervical segment sheath, and an amniotic cavity segment sheath. The vaginal segment sheath is configured to expand and support the vagina, and accommodate an external cervical segment mechanical arm of a surgical robot, and protect a vulva and vaginal wall. The cervical segment sheath is configured to expand and support a cervical canal, facilitate a passage of an intrauterine segment mechanical arm and surgical instruments of the surgical robot, and protect a cervix and cervical wall. The amniotic cavity segment sheath can pass through the amniotic cavity and extend into the amniotic cavity to protect a ruptured opening of the amniotic cavity.

Preferably, a detachable interface can be provided between the vaginal segment sheath and the cervical segment sheath for a separation and combination of the vaginal segment sheath and the cervical segment sheath. The detachable interface comprises a bolt and nut, a snap ring or snap.

Preferably, at least one camera module can be provided at a distal end of the amniotic cavity segment sheath. The camera module comprises a camera, a circuit, a lighting lamp, a power supply, and a wireless communication component, which can be configured to observe an amniotic membrane, amniotic fluid, placenta, and fetus in the amniotic cavity.

Preferably, the trans-maternal vaginal fetal membrane puncture assembly further comprises an operating table and a table side bracket.

According to an embodiment of the present invention, the trans umbilical or abdominal puncture assembly comprises a trocar and a composite sheath. The trocar includes an abdominal and uterine wall hole maker and a fetal membrane piercer. The abdominal and uterine wall hole maker is configured to make a hole in the abdominal and uterine wall. The fetal membrane piercer is configured to pierce the fetal membrane and assist the composite sheath insert into the amniotic cavity. The composite sheath comprises an abdominal and uterine wall sheath and an amniotic cavity sheath, which is configured to establish a passage through the abdominal wall, the uterine wall and the fetal membrane.

Preferably, the fetal membrane piercer comprises a handle and a drill.

Preferably, the drill comprises a first self-tapping thread, the first self-tapping thread is provided at a front end of the drill.

Preferably, a thread pitch of the first self-tapping thread is from 0.1 mm to 0.25 mm, and a thread height of the first self-tapping thread is no more than 2 mm.

Preferably, the composite sheath comprises an abdominal wall sheath and an amniotic cavity sheath. The abdominal wall sheath can be configured to expand and support the navel and/or abdominal incision, protect the navel and/or abdominal wall incision when the surgical robot intrauterine segment mechanical arm and surgical instruments pass through the navel and/or abdominal incision. The amniotic cavity sheath can pass through the amniotic cavity and extend into the amniotic cavity to protect the ruptured opening of the amniotic cavity.

Preferably, the abdominal and uterine wall sheath is configured to protect the abdominal and uterine wall incision, and facilitate the surgical robot intrauterine segment mechanical arm and surgical instruments.

Preferably, the abdominal and uterine wall sheath comprises an outer shield, the outer shield comprises a fastening component, and the fastening component is configured to rigidly connect the composite sheath to a table side bracket.

Preferably, the amniotic cavity sheath is configured to penetrate the fetal membrane and extend into the amniotic cavity to protect a fissure of the amniotic cavity.

Preferably, the amniotic cavity sheath comprises a second self-tapping thread, the second self-tapping thread is provided on a front part outer wall of the amniotic cavity sheath.

Preferably, the amniotic cavity sheath comprises a camera module, the camera module comprises a circuit, a lighting lamp, a power supply, a wireless communication component, and a plurality of cameras for observing the amniotic membrane, amniotic fluid, placenta, and fetus in the amniotic cavity.

Preferably, the trans umbilical or abdominal puncture assembly further comprises a table side bracket.

According to an embodiment of the present invention, a method for establishing a trans-maternal amniotic cavity access comprises using a trans-maternal vaginal fetal membrane puncture assembly to construct a trans-maternal vaginal amniotic cavity access, and/or using a trans umbilical or abdominal puncture assembly to construct a trans-maternal umbilical or abdominal wall amniotic cavity access.

According to an embodiment of the present invention, the using a trans-maternal vaginal fetal membrane puncture assembly to construct a trans-maternal vaginal amniotic cavity access comprises steps as follow:

S1: Expand a vagina with a vaginal speculum, insert a cervical dilator under direct vision, and inflate a balloon body of a balloon module with air or water until a diameter of a cervical dilation reaches or exceeds an expectation, for example, a cervix can pass through a cervical dilation rod with a size of 10.5 or more.

S2: Take out the cervical dilator under direct vision, insert a fetal membrane puncture instrument under a guidance of ultrasound, touches an amniotic sac, rotate the fetal membrane puncture instrument, and advance the fetal membrane puncture instrument into an amniotic cavity with a safe distance from a fetus.

S3: Under direct vision combined with an ultrasound guidance, insert a vaginal cervical dilator, pass a handle of the fetal membrane puncture instrument through a one-way valve, and place a front end of the amniotic cavity segment sheath close to the amniotic sac.

S4: Withdraw the vaginal speculum.

S5: Through ultrasonic detection and under direct vision, advance the vaginal cervical dilator, so that an amniotic cavity segment sheath enters the amniotic cavity, then exit the fetal membrane puncture instrument.

S6: Rigidly and firmly connect a fastening component to an operating table-side bracket.

Preferably, the step S1 further includes inflating the balloon body with air or water slowly.

Preferably, the step S3 further includes (1) withdrawing the vaginal speculum first, and (2) inserting the vaginal cervical dilator.

Preferably, the step S5 further includes pushing the amniotic cavity segment sheath into the amniotic cavity by a distance of 0.5 cm to 1.5 cm to ensure a safe distance from a fetus.

According to an embodiment of the present invention, the method of a transmural umbilical or abdominal puncture assembly to construct a trans-maternal abdominal wall amniotic cavity access comprises steps as follow:

S11: Choose a position of making a hole in the abdominal wall and uterine wall, if a placenta can be avoided, a navel or belly button or other parts of an abdomen are preferred, and then under a guidance of ultrasound, an abdominal and uterine wall hole maker is used to make an abdominal wall hole and uterine wall hole.

S12: Ultrasound guidance combined with direct vision, through the hole in the abdominal wall and uterine wall, insert a fetal membrane piercer, after a front end of the fetal membrane piercer touches the fetal membrane, rotate a handle of the fetal membrane piercer, and advance the fetal membrane piercer into an amniotic cavity.

S13: Insert a composite sheath into the hole through a handle of the fetal membrane piercer under ultrasonic guidance and direct vision until a front end of the composite sheath is close to the fetal membrane.

S14: Through ultrasound guidance and observation of an image captured by a camera of an amniotic cavity sheath, pull the fetal membrane piercer upward gently, and at the same time, rotate and advance the composite sheath, so that the amniotic cavity heath enters the amniotic cavity.

S15: Gently withdraw the fetal membrane piercer.

S16: Rigidly and firmly connected the composite sheath with an operating table-side bracket, or sutured and fixed the composite sheath to an abdominal skin.

Preferably, in the step S14, the amniotic cavity sheath is pushed into the amniotic cavity by a distance of 0.5 cm to 1.0 cm to ensure a safe distance from a fetus.

The trans-maternal vaginal fetal membrane puncture assembly of the present application includes a vaginal speculum, a cervical dilator, a fetal membrane puncture device, and a vaginal cervical dilator. When used together, an access for intrauterine surgical treatment of a fetus through a natural orifice of a cervix can be efficiently and safely made.

The front end of a fetal membrane puncture device in the prior art is a blunt vertebral body, when piercing the fetal membrane, because the fetal membrane wall is thin and tough, it has to rely on violence, so that the strength and advancing distance are not easy to control, which may lead to a large-scale tearing of the fetal membrane, and even accidentally injure the fetus.

The fetal membrane puncture device of the present application is provided with a self-tapping thread, so that the fetal membrane can be pierced by light rotation, and an advancing speed and distance of the fetal membrane puncture device can be precisely controlled according to a rotation speed, so as to avoid large-scale tearing of the fetal membrane and the possibility of accidental injury to the fetus.

The combined sheath can integrate a vagina, cervix and fetal membrane, which simplifies a structure of the device and improves an operation efficiency.

A front end of the amniotic segment sheath of the combined is provided with a self-tapping thread. When the vaginal cervical dilator is inserted, the self-tapping thread at the front end of the amniotic segment sheath advances, and at the same time, the front end of the fetal membrane piercer is threaded, the self-tapping thread can prevent a local fetal membrane from sliding, gently pull the fetal membrane piercer outward, and the self-tapping thread at the front end of the fetal membrane piercer can also drive the local fetal membrane to move in a direction of an operator, so that the amniotic cavity segment sheath enters the amniotic cavity more easier.

A camera module is installed at the front end of the amniotic cavity segment sheath, which can provide real-time images during a process of placing the vaginal cervical dilator, so as to avoid accidental injury to a human body under blind vision. Additionally, a situation of the amniotic membrane, amniotic fluid, placenta and fetus in the amniotic cavity can be observed dynamic.

The vaginal cervical dilator is provided with a one-way valve and a fastening component. On the one hand, the one-way valve can prevent an outflow of amniotic fluid, and at the same time, medical instruments or surgical robot arms can pass through the one-way valve freely. The fastening component can be combined with an operating table, a stent is rigidly connected, so that the vaginal cervical dilator is stably fixed, furthermore, the vaginal cervical dilator can be used as a stable and firm support point for the surgical robot arms.

The device for making an abdominal wall and amniotic cavity access of the present application includes tan abdominal and uterine wall hole maker, a fetal membrane piercer, and a composite sheath. Firstly, use the abdominal and uterine wall hole maker to make a hole in the abdominal wall and uterine wall, then use the fetal membrane piercer to insert the hole and pierce a fetal membrane, then, the composite sheath enters through the hole in the abdominal wall, uterine wall, and fetal membrane. Therefore, a channel through the abdominal wall, uterine wall and fetal membrane can be constructed efficiently and conveniently, which can be used for laparoscopic technique or surgical robot to perform intrauterine fetal surgical treatment.

The diameter of the hole in the abdominal wall, uterine wall, and fetal membrane is usually no more than 3 cm, so that a trauma to the maternal uterus is mild and a postoperative recovery is fast, thereby reducing an inducing factor of postoperative maternal uterine contraction.

The diameter of the hole in the fetal membrane is usually no more than 3 cm, which can completely avoid a placenta position, thus reducing an inducing factor of placental abruption.

The application process of the present application is simple, safe and efficient, and will provide fetal intrauterine surgery with less trauma to the mother and placenta, and fetal-friendly surgical conditions, thereby increasing the scope of fetal intrauterine surgery and improving human prenatal and postnatal care.

These and other objectives, features, and advantages of the present invention will become apparent from the following detailed description, the accompanying drawings, and the appended claims.

BRIEF DESCRIPTION OF THE DRAWINGS

In order to explain a technical solution of embodiments of the present application more clearly, there is a briefly introduction of a plurality of drawings as follow that are used in a description of the embodiment. Obviously, the drawings in the following description are only some embodiments of the present application. For those skilled in the art, other drawings can also be obtained from these drawings without any creative effort.

Furthermore, the drawing is merely a schematic illustration of the present application and is not necessarily drawn to scale. A same reference numeral in the drawing denotes the same or similar part, and thus its repeated description will be omitted. Some block diagrams shown in the drawing are functional entities, which do not necessarily correspond to physically or logically independent entities, and these functional entities may be implemented in one or more hardware modules or combinations of components.

DETAILED DESCRIPTION OF THE PREFERRED EMBODIMENT

In order to make an objective, technical solution and advantage of the present application more clearly, the present application will be further described in detail below with reference to the embodiments. It should be understood that a specific embodiment described herein is only used to explain the present application, but not to limit the present application.

It should be noted that an orientation term such as up, down, left, and right in this embodiment is only relative concept to each other or refer to a normal use state of a product, and should not be regarded as limiting.

According to an embodiment of the present invention, a device for establishing a trans-maternal amniotic cavity access can comprise a trans-maternal vaginal fetal membrane puncture assembly configured to construct a trans-vaginal amniotic cavity access, and a transmural umbilical or abdominal puncture assembly configured to construct a transmural umbilical or abdominal amniotic cavity access.

Referring to FIGS. 1 to 16, a trans-maternal vaginal fetal membrane puncture assembly according to an embodiment of the present application can comprise a vaginal speculum 100, a cervical dilator 200, a fetal membrane piercer 300, and a vaginal cervical dilator 400.

Figure 1:
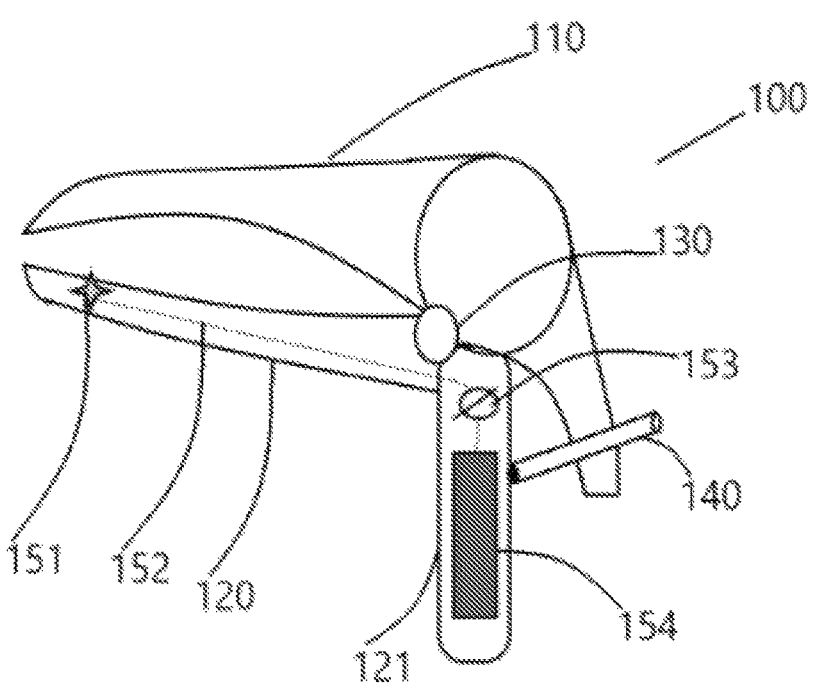
FIG. 1 is a schematic structural view of a vaginal speculum according to an embodiment of the present application.

As shown in FIG. 1, the vaginal speculum 100 according to an embodiment of the present application comprises a hand-held vaginal dilator and a light source module.

The hand-held vaginal dilator comprises an upper viewing plate 110 and a lower viewing plate 120. The upper viewing plate 110 and the lower viewing plate 120 can be hinged through a rotating shaft 130, and a rear end of the upper viewing plate 110 and the handle 121 of the lower viewing plate 120 can be provided a threaded rod 140, through which an opening and closing between the upper speculum plate 110 and the lower speculum plate 120 can be adjusted, so as to expand a vagina.

The light source module can comprise a battery 154, an LED light 151, a circuit 152, and a switch 153. The switch 153 can be disposed on the handle 121 of the hand-held vaginal dilator, and the LED light 151 can be disposed on an inner side of a front section of the lower viewing plate 120. Of course, the LED light 151 can also be replaced by a cold light source light. The hand-held vaginal dilator expands the vagina, and with the light provided by the light source module, an operator can perform cervical dilation under direct vision.

Figure 2:
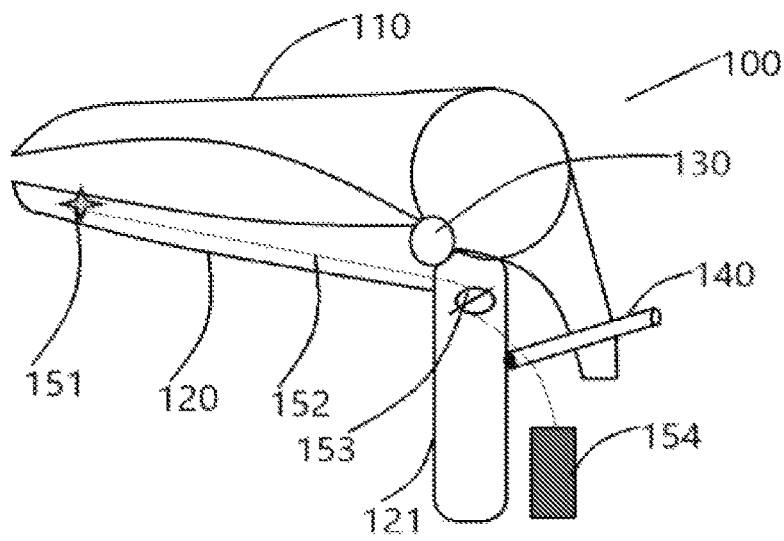
FIG. 2 is a schematic structural view of another vaginal speculum according to an embodiment of the present application.

As shown in FIG. 2, the battery 154 of the light source module of the vaginal speculum 100 according to an embodiment of the present application can also be provided independently, or can be provided with electric power by an external power source.

Figure 3:
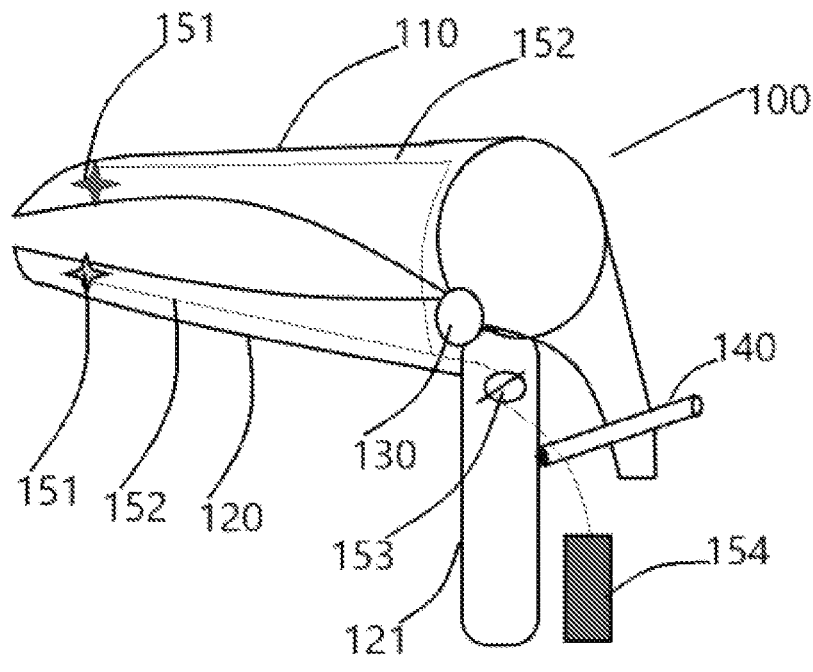
FIG. 3 is a schematic structural view of a vaginal speculum including a plurality of lamps according to an embodiment of the present application.

As shown in FIG. 3, a light source module of a vaginal speculum 100 according to an embodiment of the present application can be provided with a plurality of LED lights 151, and the LED lights 151 can be provided on an inner side of the front section of the lower speculum 120 and/or an inner side of an anterior segment of the upper speculum 110.

It can be understood that the light source module can be connected to the hand-held vaginal dilator in a detachable connection manner, for example, using sterile tape or glue to paste the LED light 151 and the circuit 152 on an upper viewing plate 110 of a conventional hand-held vaginal dilator and/or tan inner side of the lower speculum 120, the battery 154 and the switch 153 are left outside a conventional hand-held vaginal dilator, so that the conventional hand-held vaginal dilator or disposable hand-held vaginal dilator can also be used under direct vision to perform cervical dilation. Of course, a detachable light source module can also simplify a design, thereby making it a cheaper disposable product.

In addition, the hand-held vaginal dilator can also be provided with a fixing instrument by which the hand-held vaginal dilator is rigidly connected to a bedside support, allowing an operator to do other things with one hand.

Figure 4:
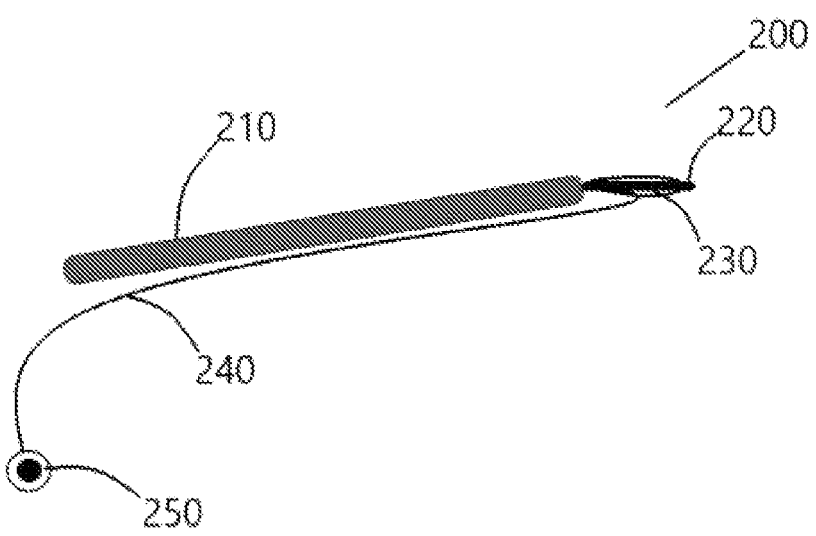
FIG. 4 is a schematic structural view of a cervical dilator according to an embodiment of the present application.

As shown in FIG. 4, a cervical dilator 200 according to an embodiment of the present application can comprise a cervical dilation rod and a balloon module. The cervical dilation rod can comprise a hand-held end 210 and a cervical dilation end 220. The balloon module can comprise a balloon body 230, a pipeline 240, and an injection pot 250. The balloon body 230 can be wrapped around and fixed on the cervical dilation end 220. The injection pot 250 has a one-way valve effect, when inject or extract air or water, the air or water injected into the balloon body 230 will not overflow. It should be noted that a diameter of the cervical dilation end 220 is usually no more than 3 mm, the balloon body 230 can be made of a medical silicone material, and a wall of the balloon body 230 is usually no more than 0.5 mm, so that the cervical dilation end 220 can be easily inserted into a maternal cervical canal when the balloon body 230 is not inflated.

Figure 5:
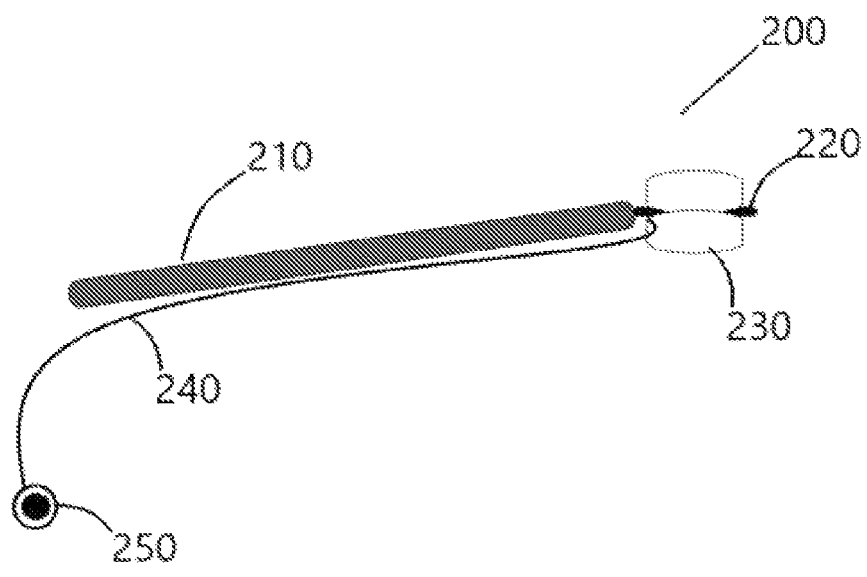
FIG. 5 is a schematic structural view of a cervical dilator after balloon inflation according to an embodiment of the present application.

As shown in FIG. 5, a syringe needle (not shown) can be inserted into the injection pot 250, air or normal saline or artificial amniotic fluid is injected, the air, normal saline or artificial amniotic fluid enters the balloon body 230 through the pipeline 240, then the balloon 230 can expand, thereby realizing cervical canal dilation. It should be noted that the medical silicone material used in the balloon body 230 can be expanded by at least 30 times in volume, so as to achieve a sufficient cervical canal dilation effect. In addition, the syringe can be replaced with a high-pressure injector to reduce the difficulty of injection.

In addition, when injecting air, normal saline or artificial amniotic fluid into the balloon body 230, it must be injected slowly and uniformly to prevent cervical damage from too fast injection.

Furthermore, a whole process of inserting the cervical dilator 200 and injecting air or normal saline or artificial amniotic fluid into the balloon body 230 can be preferably operated under direct vision and ultrasound guidance, so that a position of the cervical dilator 200 is relatively accurate. At the same time, a dynamic change of a cervix can be observed in real time, and a speed of injecting air or normal saline or artificial amniotic fluid into the balloon body 230 can be guided. If the cervix suddenly dilates rapidly, part of the air, normal saline or artificial amniotic fluid can be withdrawn to prevent permanent damage to the cervix.

Figure 6:
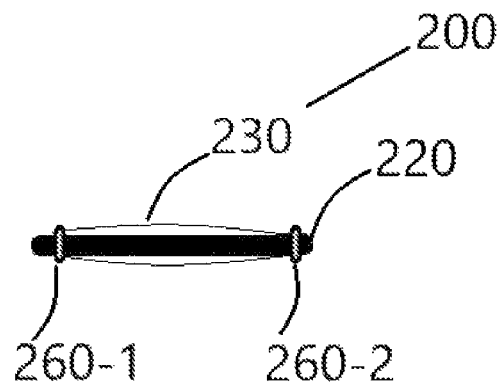
FIG. 6 is a schematic structural view of a cervical end of a cervical dilator according to an embodiment of the present application.

As shown in FIG. 6, according to an embodiment of the present application, a cervical dilation end 220 of a cervical dilator can surround with a balloon body 230, a first limit ring 260-1 and a second limit ring 260-2 can be set at a front and a rear of the cervical dilation end 220 respectively. The first limit ring 260-1 and the second limit ring 260-2 can be made of high-hardness medical silica gel, and can be fastened to the cervical dilation end 220. In addition, a position of the first limit ring 260-1 and the second limit ring 260-2 can be moved along the cervical dilation end 220 under an external force.

Due to a large difference in a length of a cervix of a mother, although it is feasible to manufacture the cervical dilator 200 with different lengths of the cervical dilation end 220, it will also cause a waste of medical resources. A technical solution of the present application can achieve precise adjustment of the length of the balloon body 230 by adjusting the first limiting ring 260-1 and the second limiting ring 260-2, so as to meet a cervical dilation requirement of different maternal cervix length, thereby avoiding waste of medical resources.

Figure 7:
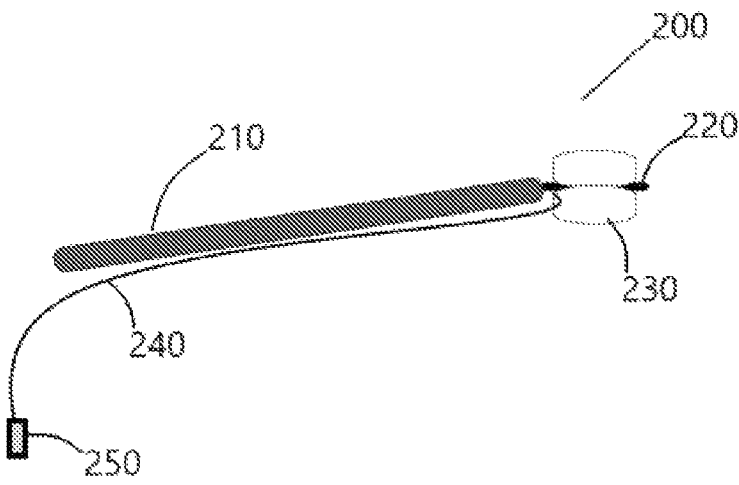
FIG. 7 is a schematic structural view of another cervical dilator according to an embodiment of the present application.

As shown in FIG. 7, a cervical dilator 200 according to an embodiment of the present application can include a cervical dilation rod and a balloon module, the cervical dilation rod can include a hand-held end 210 and a cervical dilation end 220, the balloon module can include a balloon body 230, a pipeline 240, an injection pot 250. The injection pot 250 can also adopt a rod-shaped structure, so that a needle of a syringe can be inserted deeper, so as to prevent the needle from falling out, or the needle tip overflowing air or water during an injection, thereby improving a work efficiency.

It can be understood that the cervical dilation rod can be made of high-strength polymer medical materials, or the hand-held end 210 can be made of a hollow steel tube, so as to reduce a weight of the cervical dilation rod. The pipeline 240 may adopt a thicker wall, so that when the pipeline 240 can be inflated or filled with water, the pipeline 240 is not significantly deformed.

Figure 8:
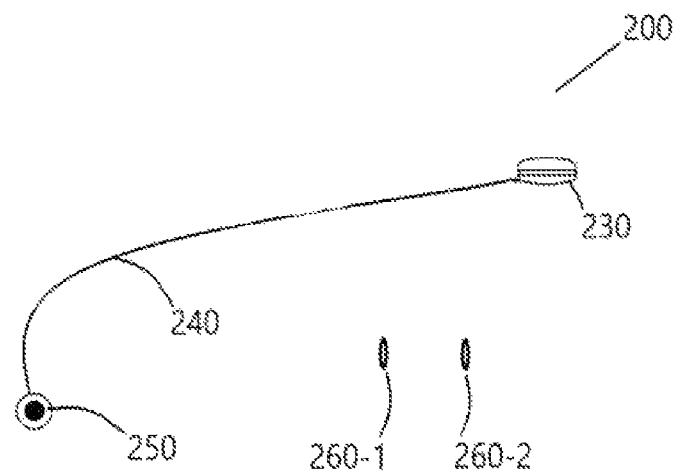
FIG. 8 is a schematic structural view of an enhanced balloon module according to an embodiment of the present application.

In addition, as shown in FIG. 8, a first limiting ring 260-1, a second limiting ring 260-2 and a balloon module can also be independently designed and manufactured to obtain an enhanced balloon module. The enhanced balloon module comprises a plurality of balloon body 230, a pipeline 240, an injection pot 250, a first limiting ring 260-1 and a second limiting ring 260-2. The enhanced balloon module can be combined with a conventional cervical dilation rod for a cervical dilation. According to a ultrasound inspection result, a length of a maternal cervical canal, a shape of an internal orifice and an external orifice of the cervical canal can be known, and a suitable conventional cervical dilation rod can be selected. Firstly, the second limiting ring 260-2 can be set at the cervical dilation end 220 of the conventional cervical dilation rod, then insert the balloon body 230, and then insert the first limit ring 260-1, adjust a distance between the first limit ring 260-1 and the second limit ring 260-2, so that a long axis length of the balloon body 230 at the dilation end 220 is consistent with an expected dilated cervical length, which can be configured to perform a cervical dilation operation.

Figure 9:
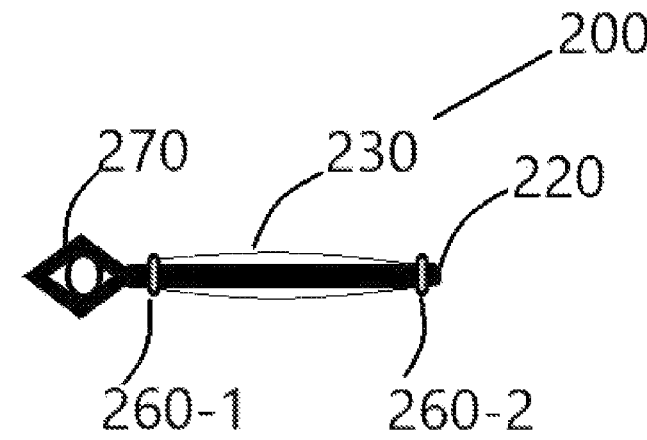
FIG. 9 is a schematic structural view of a simplified version of a cervical dilator according to an embodiment of the present application.

In addition, as shown in FIG. 9, on a basis of an aforementioned enhanced balloon module, a simplified cervical dilator 200 can also be obtained by combining with an independently cervical dilation end 220. The simplified cervical dilator 200 comprises a balloon body 230, a pipeline 240, an injection pot 250, a first limiting ring 260-1, a second limiting ring 260-2, and an independently cervical dilation end 220. A distal end of the independently cervical dilation end 220 can include an engagement part 270 which can establish a rigid connection with a handle, or be clamped by a gripping instrument. With above solution, a manufacturing cost of the simplified cervical dilator 200 can be reduced, so that the cervical dilator 200 can become a disposable instrument.

Figure 10:
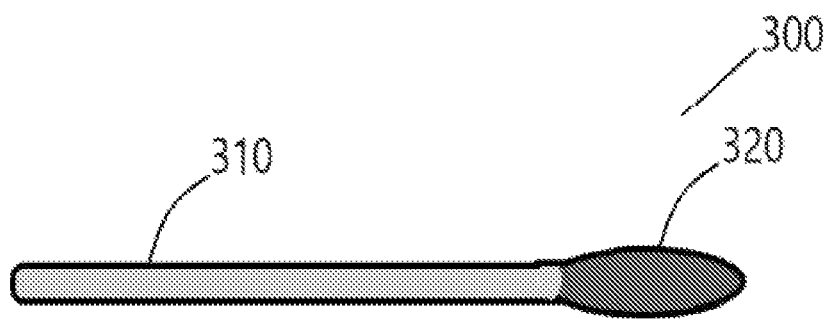
FIG. 10 is a schematic structural view of a fetal membrane piercer according to an embodiment of the present application.

As shown in FIG. 10, according to an embodiment of the present application a fetal membrane piercer 300 comprises a handle 310 and a puncture end 320. The handle 310 and the puncture end 320 can be an integrated structure or a detachable rigid connection. A length of the handle 310 is usually not less than 20 cm, the puncture end 320 can be conical, a length of the puncture end 320 is usually not less than 5 cm, and a diameter of a thickest part of a middle section of the puncture end 320 is usually not more than 2.5 cm.

Figure 11:
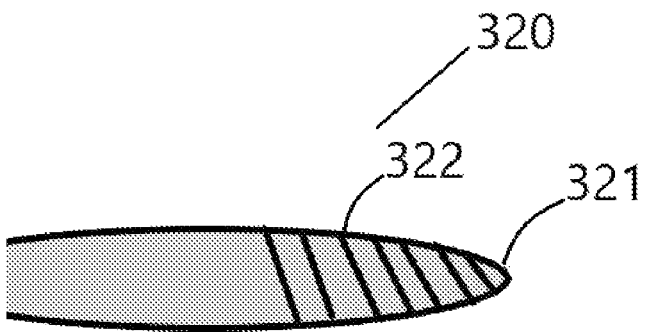
FIG. 11 is a schematic structural view of a puncture end of a fetal membrane piercer according to an embodiment of the present application.

As shown in FIG. 11, a front end 321 of the puncture end 320 of the fetal membrane piercer 300 comprises a first self-tapping thread 322, a thread spacing of the first self-tapping thread 322 is close to a thickness of a membrane wall, usually from 0.1 mm to 0.25 mm. The first self-tapping thread 322 of the fetal membrane piercer 300 can be configured to penetrate a thin and tough fetal membrane easily. After entering a amniotic cavity, the fetal membrane piercer 300 can be rotated and advanced to precisely control a depth and speed insertion of the amniotic cavity. In addition, the first self-tapping thread 322 can also assist in a vaginal cervical dilator 400 inserting into the amniotic cavity. Of course, an operation of fetal membrane puncture with the fetal membrane piercer 300 can be performed under a guidance of ultrasound, so as to ensure an accuracy of the fetal membrane puncture and not harm a fetus.

It should be noted that a thread direction of the first self-tapping thread 322 can be marked on the handle 310, the thread direction can be clockwise or counterclockwise. In addition, a foremost end of the puncture end 320 can be a sharp part of the first self-tapping thread 322. In order to avoid accidental injury to the fetus, the sharp part is usually slightly rounded and blunt. In addition, a thread height of the first self-tapping thread 322 is not more than 2 mm.

Figure 12:
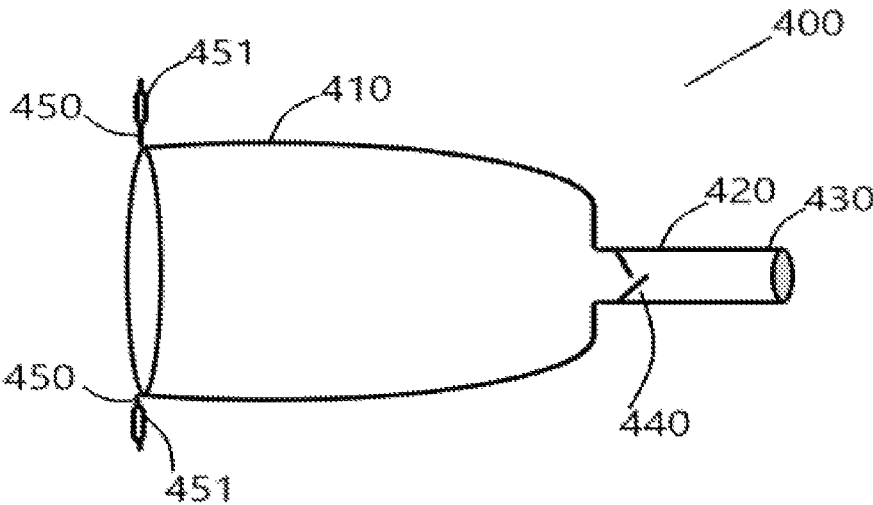
FIG. 12 is a schematic structural view of a vaginal cervical dilator according to an embodiment of the present application.

As shown in FIG. 12, according to an embodiment of the present application a vaginal cervical dilator 400 comprises a vaginal segment sheath 410, a cervical segment sheath 420, an amniotic cavity segment sheath 430, a one-way valve 440, and a shield 450. The shield 450 comprises a plurality of locking holes 451. The vaginal segment sheath 410, the cervical segment sheath 420, and the amniotic cavity segment sheath 430 can form a combined sheath for establishing a passage through the vagina, cervix, and fetal membrane. The one-way valve 440 is configured to prevent an outflow of amniotic fluid. The locking hole 451 is configured to connect with an operating table bracket 500, so as to stabilize the vaginal cervical dilator 400.

It should be noted that the vaginal segment sheath 410 is usually a cylindrical or flat cylindrical structure, its diameter is usually not less than 5 cm, and its length is usually not less than 15 cm, configured to expand and support a vagina, accommodate a surgery robotic arm, and protect a vulva and vaginal wall. The cervical segment sheath 420 is usually a cylindrical structure, its diameter is usually not less than 1.5 cm, and its length is usually not less than 2.5 cm, configured to expand and support a cervical canal, pass the surgical robotic arm and surgical instruments, and protect a cervix and cervical wall. The amniotic cavity segment sheath 430 is usually a cylindrical structure, its diameter is usually not less than 1.5 cm, and its length is usually not less than 1.0 cm, configured to pass through the amniotic cavity and extend into the amniotic cavity to protect a rupture opening of the amniotic cavity.

Figure 13:
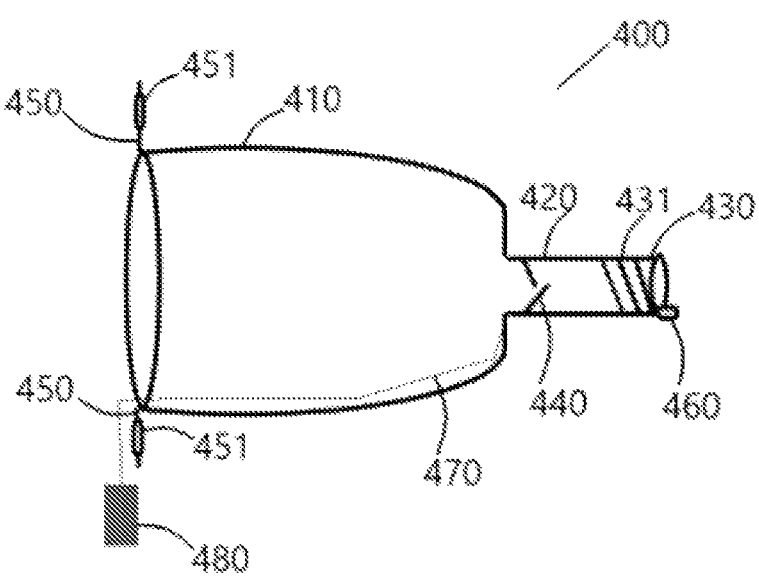
FIG. 13 is a schematic structural view of a vaginal cervical dilator including a camera module according to an embodiment of the present application.

As shown in FIG. 13, according to an embodiment of the present application a vaginal cervical dilator 400 comprises a vaginal segment sheath 410, a cervical segment sheath 420, an amniotic cavity segment sheath 430, a one-way valve 440, and a shield 450. The shield 450 comprises a plurality of locking holes 451. Wherein a front end of the amniotic cavity segment sheath 430 can include a camera module configured to observe an amniotic membrane, amniotic fluid, placenta and fetus in the amniotic cavity. The camera module comprises a camera 460, a circuit 470, an illumination lamp (not shown), a power supply 480, and a wireless communication component (not shown).

As shown in FIG. 13, according to an embodiment of the present application a vaginal cervical dilator 400 comprises a vaginal segment sheath 410, a cervical segment sheath 420, an amniotic cavity segment sheath 430, a one-way valve 440, and a shield 450. The shield 450 comprises a plurality of locking holes 451. An outer surface of a front end of the amniotic cavity segment sheath 430 comprises a second self-tapping thread 431, a thread spacing of the second self-tapping thread 431 is close to a thickness of a fetal membrane wall, usually from 0.1 mm to 0.25 mm. The second self-tapping thread 431 can enable the front end of the amniotic cavity segment sheath 430 to easily penetrate a thin and tough fetal membrane. After entering the amniotic cavity, the vaginal cervical dilator 400 can be rotated and advanced, and a depth and speed of the vaginal cervical dilator 400 can be accurately inserted into the amniotic cavity. In addition, the vaginal cervical dilator 400 can also cooperate with the fetal membrane piercer 300. For example, when the vaginal cervical dilator 400 is inserted, keeping the fetal membrane piercer 300 still or slightly pulling the fetal membrane piercer 300 outward is equivalent to an outward pushing force on the fetal membrane, and the amniotic segment sheath 430 exerts an inward pushing force and an attack force of the second self-tapping thread 431, so that the amniotic segment sheath 430 can be more easily inserted into the amniotic cavity. Of course, a placement of the vaginal cervical dilator 400 can be performed under ultrasound guidance to ensure that a fetus is not harmed.

Figure 14:
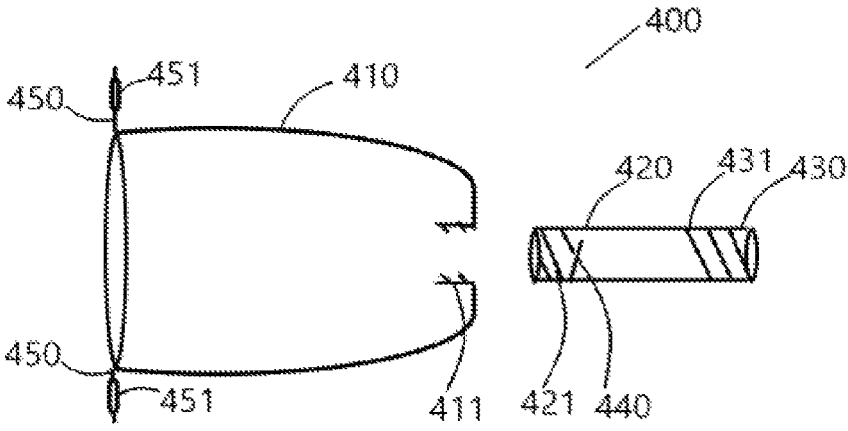
FIG. 14 is a schematic view of a detachable interface of a vaginal segment sheath and a cervical segment sheath of a vaginal cervical dilator according to an embodiment of the present application.

As shown in FIG. 14, according to an embodiment of the present application a vaginal cervical dilator 400 comprises a vaginal segment sheath 410, a cervical segment sheath 420, an amniotic cavity segment sheath 430, a one-way valve 440, and a shield 450. The shield 450 comprises a plurality of locking holes 451. The cervical segment sheath 420 and the amniotic cavity segment sheath 430 can be of an integrated structure with a detachable combined instrument. A front end of the vaginal segment sheath 410 can include a concave auxiliary cylinder, an inner wall of the concave auxiliary cylinder can include a first nut 411, a rear outer wall of the cervical segment sheath 420 can include a first bolt 421, the first bolt 421 matches the first nut 411, so that the vaginal segment sheath 410 and the cervical segment sheath 420 can be combined into a combined sheath through the first bolt 421 and the first nut. 411. In addition, by adjusting a depth of the first bolt 421 entering the first nut 411, a functional length of the cervical segment sheath 420 can be adjusted so as to adapt to a mother with different length of a cervical canal.

Figure 15:
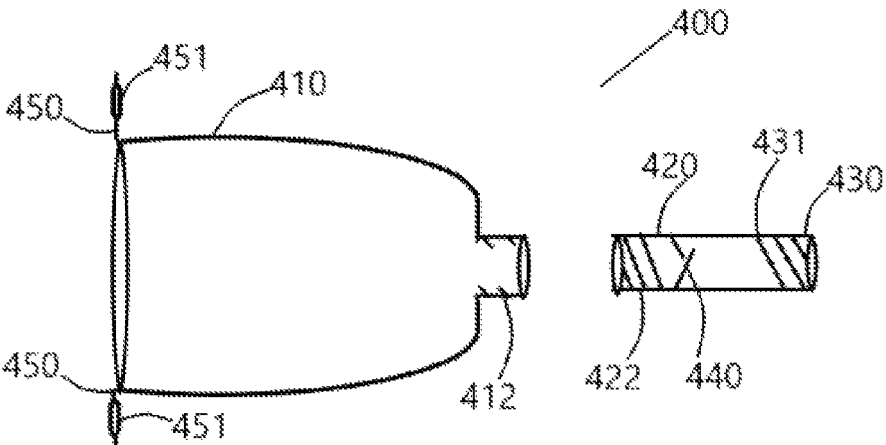
FIG. 15 is a schematic view of a detachable interface of a vaginal segment sheath and a cervical segment sheath of a second vaginal cervical dilator according to the embodiment of the present application.

As shown in FIG. 15, according to an embodiment of the present application a vaginal cervical dilator 400 comprises a vaginal segment sheath 410, a cervical segment sheath 420, an amniotic cavity segment sheath 430, a one-way valve 440, and a shield 450. The shield 450 comprises a plurality of locking holes 451. The cervical segment sheath 420 and the amniotic cavity segment sheath 430 can be of an integrated structure with a detachable combined instrument.

A front end of the vaginal segment sheath 410 can include an externally protruding auxiliary cylinder, an inner wall of the externally protruding auxiliary cylinder includes a second nut 412, a rear end outer wall of the cervical segment sheath 420 includes a second bolt 422, and the second bolt 422 is matched with the second nut 412, so that the vaginal segment sheath 410 and the cervical segment sheath 420 can be combined into a combined sheath through the second bolt 422 and the second nut 412. In addition, by adjusting a depth of the second bolt 422 entering the second nut 412, a functional length of the cervical segment sheath 420 can be adjusted so as to adapt to mothers with different lengths of a cervical canal.

Figure 16:
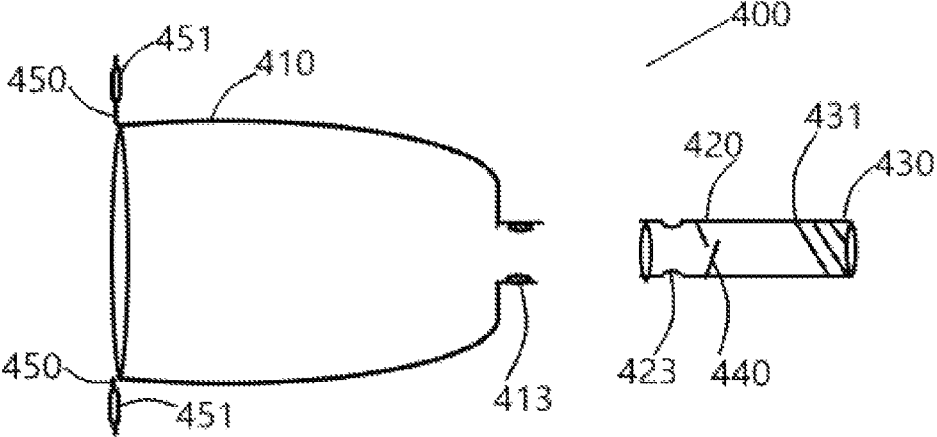
FIG. 16 is a schematic view of a detachable interface of a vaginal segment sheath and a cervical segment sheath of a third vaginal cervical dilator according to the embodiment of the present application.

As shown in FIG. 16, according to an embodiment of the present application a vaginal cervical dilator 400 comprises a vaginal segment sheath 410, a cervical segment sheath 420, an amniotic cavity segment sheath 430, a one-way valve 440, and a shield 450. The shield 450 comprises a plurality of locking holes 451. The cervical segment sheath 420 and the amniotic cavity segment sheath 430 can be of an integrated structure with a detachable combined instrument. A front end of the vaginal segment sheath 410 includes an externally protruding auxiliary cylinder, an inner wall of the externally protruding auxiliary cylinder includes a plurality of convex points 413, and a rear outer wall of the cervical segment sheath 420 includes a plurality of concave rings 423, the convex point 413 can matches the concave ring 423, so that the vaginal segment sheath 410 and the cervical segment sheath 420 can be rigidly connected through the convex point 413 and the concave ring 423 to form a combined sheath.

Figure 17:
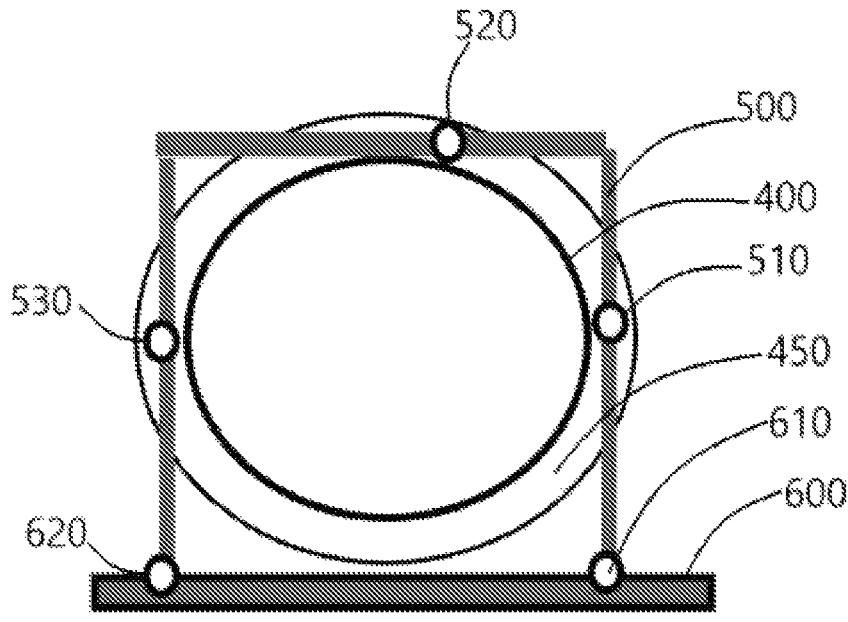
FIG. 17 is a schematic view of a connection structure between a vaginal cervical dilator and an operating table-side bracket according to an embodiment of the present application.

Referring to FIG. 17, a vaginal cervical dilator 400 according to an embodiment of the present application can be rigidly connected to a table side bracket 500 and an operating table 600. As shown in FIG. 17, the trans-maternal vaginal fetal membrane puncture assembly further include a table side bracket 500 and an operating table 600. The table side bracket 500 can establish a rigid and stable connection with the operating table 600 through a first fastening component 610, a second fastening component 620. The table-side bracket 500 can be connected by a third fastening component 510, a fourth fastening component 520, and a fifth fastening components 530 respectively with a plurality of lock holes 451 on a shield 450 of a vaginal cervical dilator 400 to establish rigid and stable connections. In this way, a rigid and stable connection between the vaginal cervical dilator 400, the table side bracket 500, and the operating table 600 can be achieved, furthermore, the vaginal cervical dilator 400 can provide a stable point of support for a robotic arm and/or a medical device that needs to enter an amniotic cavity to perform a fetal surgical treatment.

It should be noted that, a plurality of locking holes 451 on the shield 450 of the vaginal cervical dilator 400 are usually left a space to allow the third fastening component 510, the fourth fastening component 520, and the fifth fastening component 530 to move within a certain range. There is usually a space on the operating table 600 to allow the first fastening component 610 and the second fastening component 620 to move and adjust within a certain range. In addition, the table side bracket 500 can be square, rectangular, circular or oval, if the table side bracket 500 is a square or rectangular structure, a distance between each frame is allowed to move and adjust within a certain range; if the table side bracket 500 is a circular or elliptical structure, its inner diameter is allowed to move and adjust within a certain range, so as to adapt to different specifications of the vaginal cervical dilator 400 and meet a need of different body types.

A process of the trans-maternal vaginal fetal membrane puncture assembly for making a vaginal cervix amniotic cavity access according to an embodiment of the present invention comprises steps as follow.

S1: After an anesthesia is successful, a doctor sterilizes and spreads a towel, expands a vagina with a vaginal speculum, and examines a vagina and external cervical orifice with a help of a vaginal speculum.

S2: The doctor pulls a front lip of the external cervical orifice with forceps, and inserts a suitable cervical dilator from the external cervical orifice to a cervical canal under direct vision. Under a guidance of ultrasound, a balloon body of a cervical dilator is completely located in a cervix that is expected to be dilated, then the balloon body is inflated or filled with water until a degree of cervical canal dilation reaches or exceeds an expectation which can be monitored in real time. The degree of cervical canal dilation depends on an outer diameter of a cervical sheath in which a vaginal cervical dilator is expected to be placed. An inner diameter of the cervical canal is usually more than 1.5 cm after dilation, so as to pass through a conventional cervical dilation rod with a size of 10.5 or more.

S3: The doctor takes out the cervical dilator under direct vision, inserts a fetal membrane piercer under the guidance of ultrasound, when an amniotic sac can be touched, rotates the fetal membrane piercer, and advances fetal membrane piercer into an amniotic cavity with a pushing distance ranged from 0.5 cm to 1.5 cm to ensure a safe distance from a fetus.

S4: Under direct vision combined with ultrasound guidance, a vaginal cervical dilator is inserted, a handle of the fetal membrane piercer is passed through a one-way valve and an amniotic cavity segment sheath to approach the amniotic sac.

S5: The vaginal speculum is withdrawn.

S6: Through ultrasonic detection and camera observation, the doctor rotates and advances the vaginal cervical dilator, and at the same time, gently pulls the fetal membrane piercer outward, and punctures a fetal membrane with a self-tapping thread of the amniotic cavity segment sheath so that the amniotic cavity segment sheath can enter into an amniotic cavity, and then reverses a rotation of the fetal membrane piercer so that the fetal membrane piercer can be completely withdrawn.

S7: Finally, the doctor completes a rigid and stable connection among the vaginal cervical dilator, a table side bracket, and an operating table.

It should be noted that in step S2, the balloon body can be inflated or filled with water slowly. When the cervical canal is observed to dilate suddenly and rapidly, the balloon body inflation or water filling can be suspended, or part of air or water in the balloon body should be extracted to avoid cervical damage.

In addition, in step S4, the vaginal speculum can also be withdrawn while the vaginal cervical dilator is inserted. In step S6, the amniotic cavity segment sheath of the vaginal cervical dilator is usually pushed into the amniotic cavity by a distance of 0.5 cm to 1.5 cm to ensure a safe distance from the fetus.

According to an embodiment of the present invention, a device for making access to an abdominal wall and amniotic cavity can include a puncture device and a composite sheath. The puncture device can include an abdominal wall uterine wall hole maker and a fetal membrane piercer. The abdominal wall uterine wall hole maker can be configured to make holes in the abdominal wall and uterine wall, the fetal membrane piercer can be configured to pierce the fetal membrane, and can assist the composite sheath to be inserted into an amniotic cavity to build an access through the abdominal wall, the uterine wall and the fetal membrane.

Figure 18:
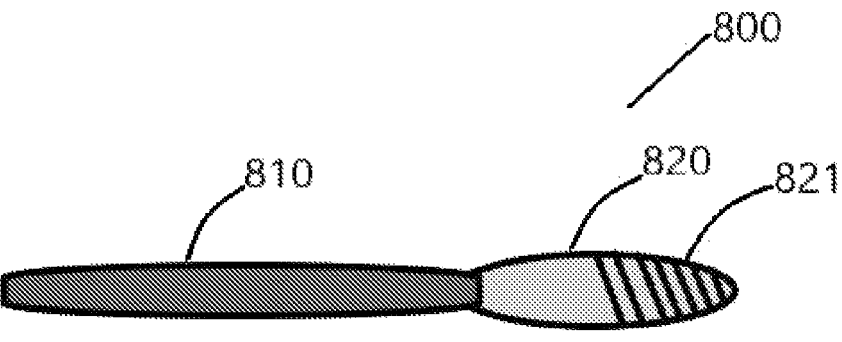
FIG. 18 is a schematic structural view of a fetal membrane piercer according to an embodiment of the present application.
Figure 19:
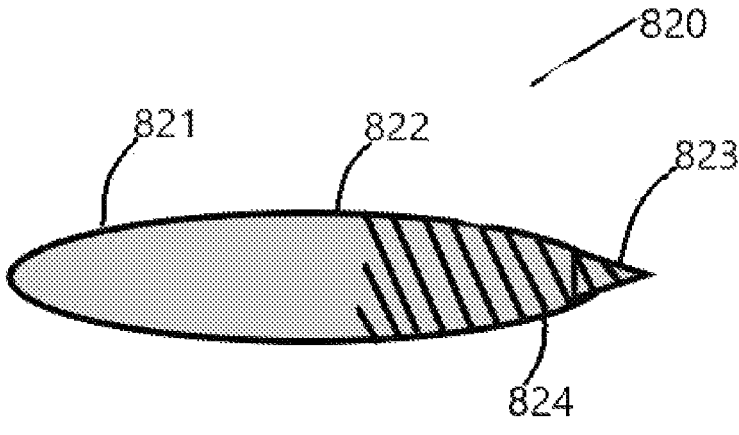
FIG. 19 is a schematic structural view of a drill of a fetal membrane piercer according to an embodiment of the present application.

Referring to FIGS. 18 and 19, a fetal membrane piercer according to an embodiment of the present application can be configured to make holes in the fetal membrane.

As shown in FIG. 18, a fetal membrane piercer 800 according to an embodiment of the present application comprises a handle 810 and a drill 820. The handle 810 and the drill 820 can be an integrated structure, and the handle 810 and the drill 820 can also be detachable and combinable independent components, which usually be made of stainless steel, titanium alloy or polymer engineering plastics.

The handle 810 can be a round rod-shaped structure, with a diameter of usually not more than 1 cm, and a length of usually not less than 15 cm.

As shown in FIG. 19, a drill 820 of a fetal membrane piercer 800 according to an embodiment of the present application comprises a tip portion 821, a body portion 822, and a tail portion 823. There is a first self-tapping thread 824 on a surface of the body portion 822 and the tail portion 823, with a thread pitch of 0.1 mm to 0.25 mm, and a thread height of no more than 2 mm. In addition, the thread rotation direction of the first self-tapping thread 824 can be markedly marked on the handle 810, which is convenient for doctors to refer to during operation.

A length of the drill 820 is usually no more than 2.5 cm, wherein the tip portion 821 is a conical structure with a length of usually no more than 0.5 cm. A length of the body portion 822 is usually no more than 1.5 cm, and a length of the tail portion 823 is usually no more than 0.5 cm. A segment of the body portion 822 is usually round and smooth in structure, with a diameter of not less than 1.5 cm at a thickest part.

A doctor can gently rotate the handle 810 with reference to a rotation direction of the first self-tapping thread 124 marked on the handle 810 to puncture a fetal membrane by the first self-tapping thread 824 of the tip 810 and the body, and then inserts the drill 820 into an amniotic cavity.

Figure 20:
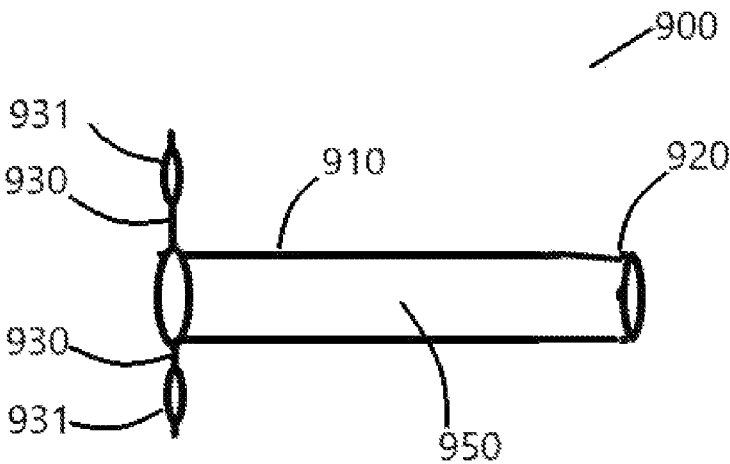
FIG. 20 is a schematic structural view of a composite sheath according to an embodiment of the present application.
Figure 21:
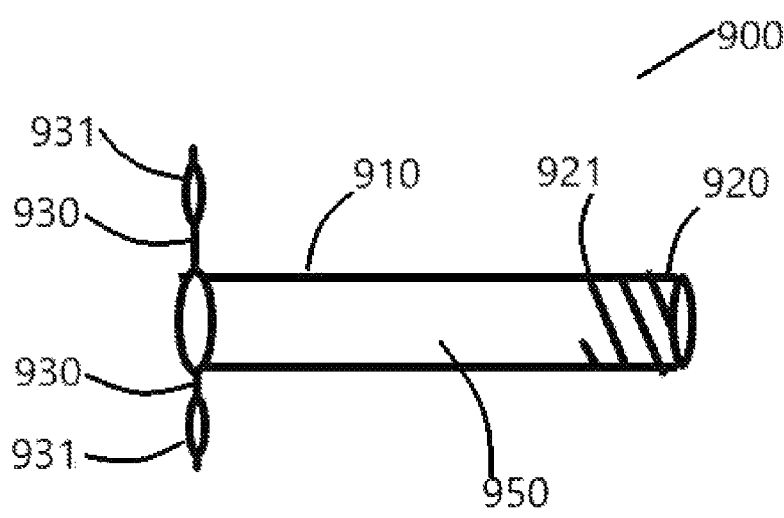
FIG. 21 is a schematic structural view of an amniotic cavity sheath according to an embodiment of the present application.
Figure 22:
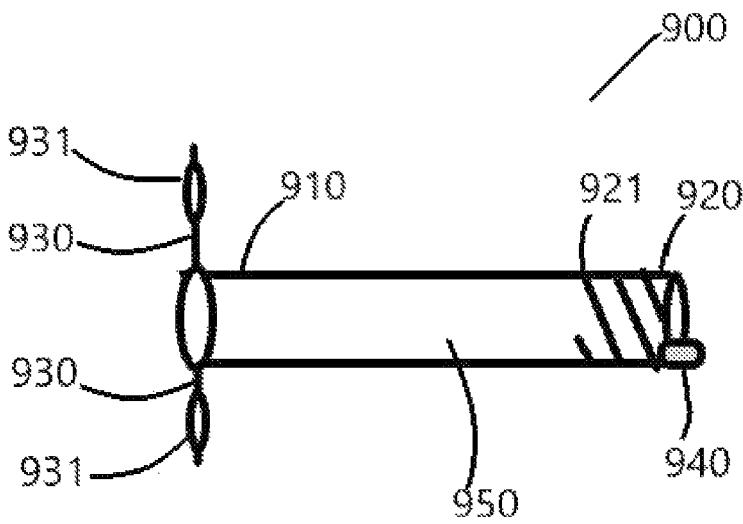
FIG. 22 is a schematic structural view of another amniotic cavity sheath according to an embodiment of the present application.

Referring to FIGS. 20 to 22, a composite sheath according to an embodiment of the present application can be configured to enter an amniotic cavity through an umbilicus or abdomen to make a trans abdominal and/or uterine wall amniotic cavity access.

As shown in FIG. 20, the composite sheath 900 according to an embodiment of the present application comprises an abdominal wall sheath 910, an amniotic cavity sheath 920, a shield 930, and a sheath cavity 950, the shield 930 can be disposed on the abdominal wall. At an end of the abdominal wall sheath 910, the shield 930 can be in s shape of a leaflet or a disk. The shield 930 can be provided with a plurality of locking holes 931, which can be configured to suture fix or connect with a lock.

The abdominal wall sheath 910 and the amniotic cavity sheath 920 are usually cylindrical. The abdominal wall sheath 910 is usually with a length of not less than 5 cm, the amniotic cavity segment sheath 920 is usually with a length of not less than 1 cm, and the sheath cavity 950 is usually with an inner diameter of not less than 1.5 cm. The abdominal wall sheath 910 can be configured to expand and support a hole of the abdominal wall and the uterine wall, accommodate a surgical robot arm, and protect the abdominal wall and the uterine wall. The amniotic cavity sheath 920 can be configured to expand and support a fetal membrane hole, pass through an intrauterine mechanical arm of the surgical robot and surgical instruments, and protect a fetal membrane wound.

Of course, the composite sheath 900 can also be provided with multiple specifications and models according to the length of the abdominal wall sheath 910 and the amniotic cavity sheath 920 and the inner diameter of the sheath cavity 950 so as to meet a need of different human bodies and surgical robot arms.

As shown in FIG. 21, a composite sheath 900 according to an embodiment of the present application comprises an abdominal wall sheath 910, an amniotic cavity sheath 920, a shield 930, and a sheath cavity 950. The shield 930 can be provided with a plurality of lock holes 931. Wherein the amniotic cavity sheath 920 comprises a second self-tapping thread 921 with a thread spacing close to a thickness of a fetal membrane wall of 0.1 mm to 0.25 mm. The second self-tapping thread 921 can make a front end of the amniotic cavity sheath 920 easily penetrate a thin and tough fetal membrane. After entering an amniotic cavity, the composite sheath 900 can be rotated and advanced, and inserted into the amniotic cavity with a depth and speed of the composite sheath 900 being precisely adjusted.

In addition, an operation of inserting the composite sheath 900 can also be cooperated with the fetal membrane piercer 800. For example, when the composite sheath 900 is inserted, keeping the fetal membrane piercer 800 still or slightly pushing the fetal membrane piercer 800 upward can be equivalent to an outward pushing force to puncture the fetal membrane, plus the amniotic cavity segment sheath 920 exerting an inward pushing force and an attack force of the second self-tapping thread 921, so as to enable the amniotic cavity segment sheath 920 more easily insert into the amniotic cavity. Of course, an inserting operation of the composite sheath 900 can be performed under ultrasound guidance to ensure that the fetus is not harmed.

As shown in FIG. 22, a composite sheath 900 according to an embodiment of the present application comprises an abdominal wall sheath 910, an amniotic cavity sheath 920, a shield 930, and a sheath cavity 950. The shield 930 can be provided with a plurality of lock holes 931. The composite sheath 900 can include a camera module 940, the camera module 940 comprises a camera, a circuit, a lighting lamp, a power supply, and a wireless communication component, wherein the camera can be arranged at a front end of the amniotic cavity sheath 920 configured to observe the amniotic membrane of intracavitary amniotic membrane, amniotic fluid, placenta, and fetal condition in real time.

Figure 23:
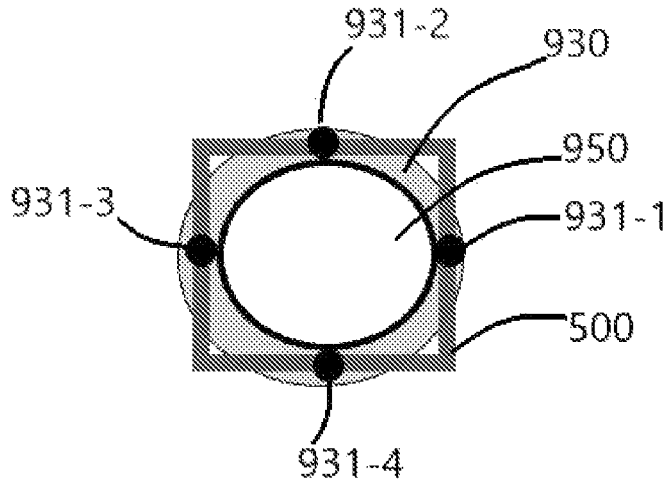
FIG. 23 is a schematic structural view of a connection between a composite sheath and a bedside support according to an embodiment of the present application.
Figure 24:
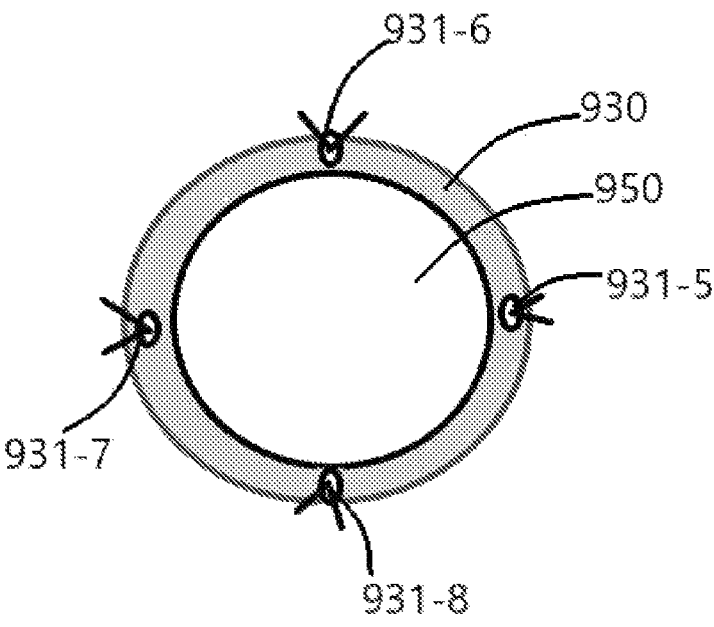
FIG. 24 is a schematic structural view of a composite sheath fixed to an abdominal skin according to an embodiment of the present application.

Referring to FIGS. 23 and 24, a solution of a fixed connection a composite sheath 900 according to an embodiment of the present application is shown.

As shown in FIG. 23, a device for making a trans abdominal wall and amniotic cavity wall access further comprises a table side bracket 500 and an operating table (not shown). Wherein the table side bracket 500 can be rigidly connected with the operating table (not shown), the table side bracket 500 can also pass through a first fastening component 931-1, a second fastening component 931-2, a third fastening component 931-3 and a fourth fastening component 931-4 to establish a rigid and stable connection with a plurality of lock holes 931 on a corresponding outer shield 930. In this way, the rigid and stable connection of the composite sheath 900, the table side bracket 500 and the operating table (not shown) can be realized, thereby the composite sheath 900 being able to provide a stable support point for a surgical robot arm and medical instruments that need to enter the amniotic cavity to perform a fetal surgical treatment.

It should be noted that, there is a space left in a plurality of lock holes 931 to allow the first fastening component 931-1, the second fastening component 931-2, the third fastening component 931-3 and the fourth fastening component 931-4 movable within a certain range. In addition, the table side bracket 500 can have a square, rectangular, circular or oval structure. If the table side bracket 500 has a square or rectangular structure, a distance between each frame can be adjusted within a certain range, and if the table side bracket 500 has a circular or elliptical structure, an inner diameter can be allowed a movement and adjustment within a certain range, so as to adapt to the composite sheath 900 with different specifications and meet a need of a human body with different sizes.

As shown in FIG. 24, after a composite sheath 900 being inserted into an abdominal and uterine wall and an amniotic cavity, a lock hole 931-5, a lock hole 931-6, a locking hole 931-7 and a locking hole 931-8 of a shield 930 of the composite sheath 900 can be sutured and fixed to an abdominal skin of a mother through sutures, so as to achieve a fixation of the composite sheath 900.

An embodiment of the present application provides a process for making a tans abdominal wall and uterine wall amniotic cavity access including steps as follow.

S11: A doctor selects and marks a position of an abdominal wall and a uterine wall for making a hole, then uses an abdominal wall uterine wall hole maker to make an abdominal wall hole and a uterine wall hole under a guidance of ultrasound.

In step S11, the doctor can use ultrasonic equipment to observe a fetal, amniotic fluid, and placenta. If the placenta can be avoided being injury, a maternal belly button or beside belly button can be preferred as a perforation site. If the placenta is directly opposite the maternal belly button or beside the belly button, other part of an abdomen can be selected as the perforation site.

It is a usually necessary to select an appropriate type of the abdominal wall uterine wall hole maker with reference to an expected size of an abdominal wall hole and uterine wall hole and a thickness of the maternal abdominal wall.

S12: Ultrasound guidance combined with direct vision, the doctor inserts a fetal membrane piercer through the hole in the abdominal wall and the hole in the uterine wall, rotates a handle of the fetal membrane piercer, and advances the fetal membrane piercer into an amniotic cavity.

In step S12, when rotating the feal membrane piercer, the doctor can gently twist the handle of the fetal membrane piercer, observe an advancement of a tip of a drill at all times, so as to ensure a safe distance from a fetus, and avoid accidental injury to the fetus.

It is usually necessary to select an appropriate type of the fetal membrane piercer with reference to an expected size of an abdominal wall hole and/or uterine wall hole and a thickness of a maternal abdominal wall.

S13: The doctor inserts a composite sheath into the abdominal wall hole and/or the uterine wall hole through the handle of the fetal membrane piercer under ultrasonic guidance and direct vision until a front end of the composite sheath is close to the fetal membrane.

It is usually necessary to select an appropriate size of the composite sheath with reference to an expected size of an abdominal wall hole and/or a uterine wall hole and a thickness of the maternal abdominal wall.

S14: The doctor gently pulls the fetal membrane piercer upward, and at the same time, rotates and advances the composite sheath through ultrasound guidance and observation of an image captured by a camera at a front end of an amniotic cavity sheath, so that the amniotic cavity sheath can enter an amniotic cavity.

Usually, the amniotic cavity sheath can be pushed into the amniotic cavity by a distance of 0.5 cm to 1.0 cm to ensure a safe distance from the fetus.

S15: The doctor fixes the composite sheath with one hand, and gently withdraws the fetal membrane piercer with the other hand.

S16: The doctor performs a rigidly and firmly connection between the composite sheath with a table side bracket, or sutures the composite sheath on a maternal abdominal skin.

The above are only examples of the present application, and do not limit a technical scope of the present application. Therefore, any minor modifications, equivalent changes and modifications made to the above embodiments according to a technical essence of the present application still belong to the present application, within the scope of the technical solution. Professionals should appreciate that skilled artisans may implement a described functionality using different methods for each particular application, but such implementations should not be considered beyond the scope of this application.

What is claimed is:

1. A device for establishing a trans-maternal amniotic cavity access to implement an intrauterine fetal minimally invasive surgery, comprising:
   a trans-maternal vaginal fetal membrane puncture assembly configured to construct a transvaginal amniotic cavity access,
   a trans-maternal abdominal wall uterine fetal member puncture assembly configured to construct a trans umbilical and/or abdominal wall amniotic cavity access, and
   an amniotic cavity combined sheath configured to form the amniotic cavity access,
   wherein the trans-maternal vaginal fetal membrane puncture assembly comprises:
   a vaginal speculum configured to expand a vagina and perform a cervical dilation operation under a direct vision, the vaginal speculum includes a hand-held vaginal dilator and a light source module,
   a cervical dilator configured to improve an efficiency of a cervical dilation, the cervical dilator includes a cervical dilation rod and a balloon module,
   a fetal membrane puncture instrument configured to pierce a fetal membrane, and
   a vaginal cervical dilator configured to form a passage through a vagina, cervix, and fetal membrane, the vaginal cervical dilator includes a combined sheath, a one-way valve, and a fastening component.

2. The device according to claim 1, wherein the light source module comprises a battery, a light-emitting diode lamp, a circuit, and a switch.

3. The device according to claim 2, wherein the light source module is connected to a hand-held vaginal dilator in a detachable coupling manner, so that a conventional hand-held vaginal dilator can be used as a vaginal speculum.

4. The device according to claim 1, wherein the balloon module comprises a balloon body, a pipeline, and an injection pot, the balloon body is wrapped around and fixed on the cervical dilation rod, and the injection pot is configured to connect a syringe needle.

5. The device according to claim 1, wherein the fetal membrane puncture instrument comprises a handle and a puncturing part, the puncture part is conical with a self-tapping thread.

6. The device according to claim 1, wherein the combined sheath comprises:
   a vaginal segment sheath configured to expand and support the vagina and protect a vulva and vaginal wall,
   a cervical segment sheath configured to expand and support a cervical canal and facilitate a passage of an intrauterine surgical robotic arm, and
   an amniotic cavity segment sheath configured to protect a ruptured opening of the amniotic cavity.

7. The device according to claim 6, wherein the combined sheath further comprises:
   a detachable interface configured to separate and combine the vaginal segment sheath and the cervical segment sheath, the detachable interface includes a bolt and nut, and a snap ring and snap.

8. The device according to claim 6, wherein the combined sheath further comprises:
   a camera module configured to observe an amniotic membrane, amniotic fluid, placenta, and fetus in the amniotic cavity, the camera module includes a camera, a circuit, a lighting lamp, a power supply, and a wireless communication component.

9. The device according to claim 6, wherein the combined sheath further comprises:
   a second self-tapping thread being provided on a front part outer wall of the amniotic cavity sheath configured to assist in puncturing a fetal membrane.

10. A device for establishing a trans-maternal amniotic cavity access to implement an intrauterine fetal minimally invasive surgery, comprising:
   a trans-maternal vaginal fetal membrane puncture assembly configured to construct a transvaginal amniotic cavity access,
   a trans-maternal abdominal wall uterine fetal member puncture assembly configured to construct a trans umbilical and/or abdominal wall amniotic cavity access, and
   an amniotic cavity combined sheath configured to form the amniotic cavity access,
   wherein the trans-maternal abdominal wall uterine fetal member puncture assembly comprises:
   a trocar configured to make a hole in an abdominal wall and uterine wall,
   a fetal membrane piercer configured to pierce the fetal membrane, and
   a composite sheath configured to establish a passage through the abdominal wall, the uterine wall and the fetal membrane,
   wherein the fetal membrane piercer comprises a handle and a drill, the drill includes a first self-tapping thread, the first self-tapping thread is provided at a front end of the drill.

11. A device for establishing a trans-maternal amniotic cavity access to implement an intrauterine fetal minimally invasive surgery, comprising:
   a trans-maternal vaginal fetal membrane puncture assembly configured to construct a transvaginal amniotic cavity access, a trans-maternal abdominal wall uterine fetal member puncture assembly configured to construct a trans umbilical and/or abdominal wall amniotic cavity access, and
   an amniotic cavity combined sheath configured to form the amniotic cavity access,
   wherein the trans-maternal abdominal wall uterine fetal member puncture assembly comprises:
   a trocar configured to make a hole in an abdominal wall and uterine wall,
   a fetal membrane piercer configured to pierce the fetal membrane, and
   a composite sheath configured to establish a passage through the abdominal wall, the uterine wall and the fetal membrane,
   wherein the composite sheath comprises:
   an abdominal and uterine wall sheath configured to expand and support at least one of a navel and an abdominal incision, and
   an amniotic cavity sheath configured to penetrate the fetal membrane and extend into the amniotic cavity,
   wherein the abdominal and uterine wall sheath further comprises a shield configured to connect with a bracket and an operating table, the shield includes a fastening component.

12. A device for establishing a trans-maternal amniotic cavity access to implement an intrauterine fetal minimally invasive surgery, comprising:
   a trans-maternal vaginal fetal membrane puncture assembly configured to construct a transvaginal amniotic cavity access,
   a trans-maternal abdominal wall uterine fetal member puncture assembly configured to construct a trans umbilical and/or abdominal wall amniotic cavity access, and
   an amniotic cavity combined sheath configured to form the amniotic cavity access,
   wherein the trans-maternal abdominal wall uterine fetal member puncture assembly comprises:
   a trocar configured to make a hole in an abdominal wall and uterine wall,
   a fetal membrane piercer configured to pierce the fetal membrane, and
   a composite sheath configured to establish a passage through the abdominal wall, the uterine wall and the fetal membrane,
   wherein the composite sheath comprises:
   an abdominal and uterine wall sheath configured to expand and support at least one of a navel and an abdominal incision, and
   an amniotic cavity sheath, configured to penetrate the fetal membrane and extend into the amniotic cavity, comprising a second self-tapping thread configured to assist in puncturing a fetal membrane.

13. The device according to claim 12, wherein the amniotic cavity sheath further comprises:
   a camera module configured to observe an amniotic membrane, amniotic fluid, placenta, and fetus in the amniotic cavity, the camera module includes a circuit, a lighting lamp, a power supply, a wireless communication component, and a plurality of cameras.

* * * * *